(12) United States Patent
Stewart, Sr.

(10) Patent No.: US 6,203,530 B1
(45) Date of Patent: Mar. 20, 2001

(54) AUTO-INJECTION DEVICE

(75) Inventor: Edward Stewart, Sr., Dodge City, KS (US)

(73) Assignee: Pos-T-Vac, Inc., Dodge City, KS (US)

( * ) Notice: Subject to any disclaimer, the term of this patent is extended or adjusted under 35 U.S.C. 154(b) by 0 days.

(21) Appl. No.: 08/789,839

(22) Filed: Jan. 28, 1997

(51) Int. Cl.$^7$ .................................................. A61M 5/00
(52) U.S. Cl. .............................................................. 604/207
(58) Field of Search .................................... 604/117, 192, 604/198, 207, 208, 263, 68, 70, 72, 131, 133, 134–138, 144, 156, 157, 162, 181, 187

(56) References Cited

U.S. PATENT DOCUMENTS

| | | | |
|---|---|---|---|
| 1,845,930 | * | 2/1932 | Morrow ................................ 604/157 |
| 2,585,815 | | 2/1952 | McLintock . |
| 2,695,023 | | 11/1954 | Brown . |
| 2,902,994 | * | 9/1959 | Scherer ................................... 604/68 |
| 3,880,163 | * | 4/1975 | Ritterskamp . |
| 4,150,669 | | 4/1979 | Latorre . |
| 4,592,745 | | 6/1986 | Rex et al. . |
| 5,114,406 | | 5/1992 | Gabriel et al. . |
| 5,137,516 | | 8/1992 | Rand et al. . |
| 5,320,609 | * | 6/1994 | Haber et al. ........................... 604/137 |
| 5,358,489 | | 10/1994 | Wyrick . |
| 5,425,715 | * | 6/1995 | Dalling et al. . |
| 5,480,387 | * | 1/1996 | Gabriel et al. ........................ 604/156 |
| 5,514,097 | * | 5/1996 | Knauer ................................... 604/136 |
| 5,637,094 | * | 6/1997 | Stewart, Jr. et al. ................. 604/157 |
| 5,681,291 | * | 10/1997 | Galli ....................................... 604/192 |
| 5,709,662 | * | 1/1998 | Olive et al. ........................... 604/157 |

FOREIGN PATENT DOCUMENTS 9413342   6/1994   (WO) .

OTHER PUBLICATIONS

Photocopy of container for "Autopen AN 3000" by Owen Mumford.
Brochure by Medis entitled "Painpen".

* cited by examiner

Primary Examiner—Sharon Kennedy
Assistant Examiner—Ann Lam
(74) Attorney, Agent, or Firm—Hovey, Williams, Timmons & Collins

(57) ABSTRACT

An auto-injection device is provided for mounting a standard medical syringe which enables the user to automatically inject the contents of the syringe to a desired penetration depth. The auto-injection device includes a barrel sized for receiving the syringe therein, a driver shiftably received in the barrel for moving the syringe and causing injection of its contents, and a trigger accessible from outside the syringe, the trigger requiring movement across the exterior surface of the barrel prior to depression for releasing the plunger as a safety against inadvertent needle exposure and discharge. The barrel may include a window for enabling the user to ascertain whether the device is cocked or not. The barrel may be provided in two separate sections with one of the sections receivable into the other to permit cocking. The barrel also may include a slot for receiving a button to permit exposure of the needle to remove a protective cap when the device is cocked and the syringe is withdrawn into the barrel.

20 Claims, 2 Drawing Sheets

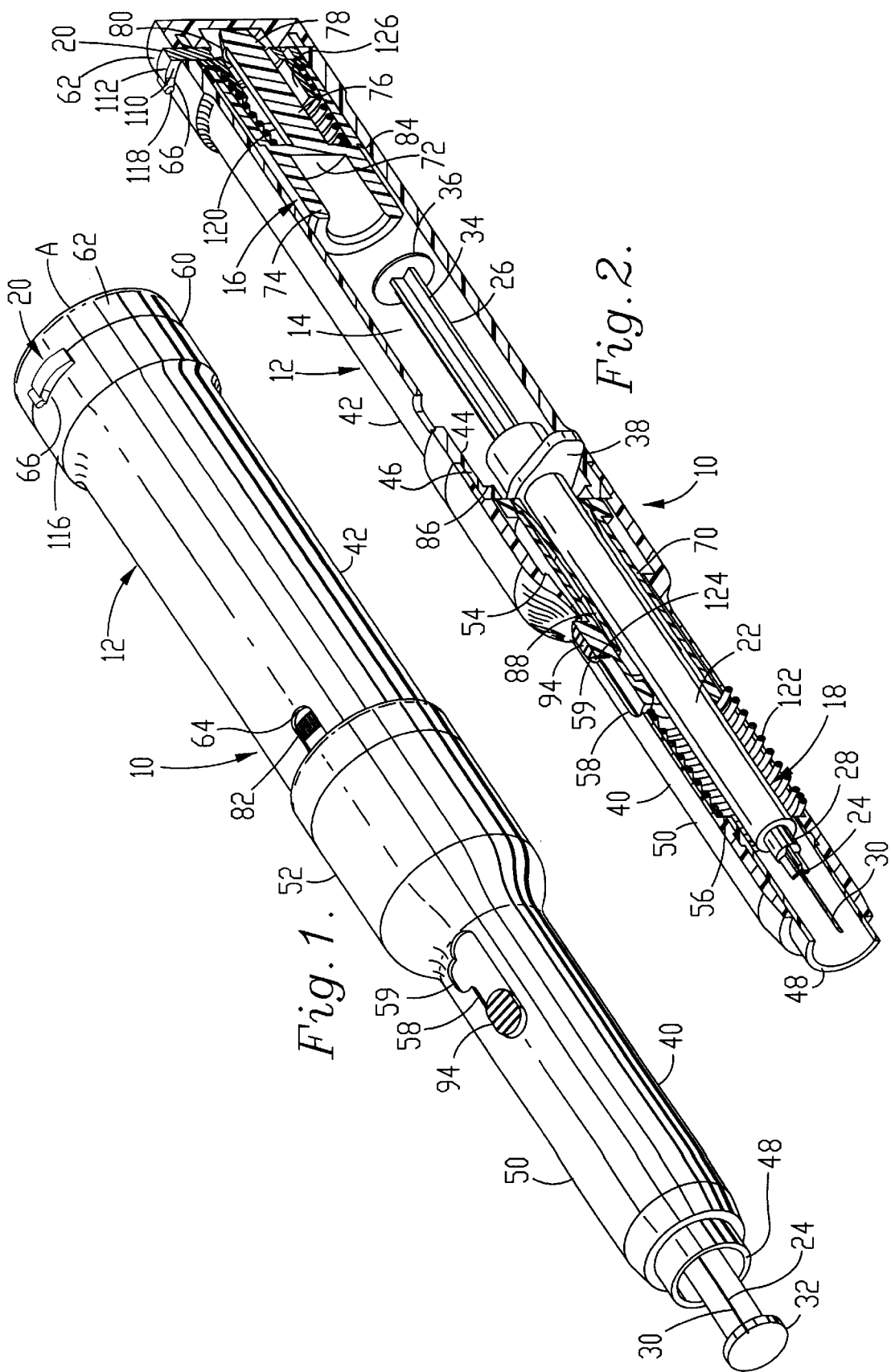

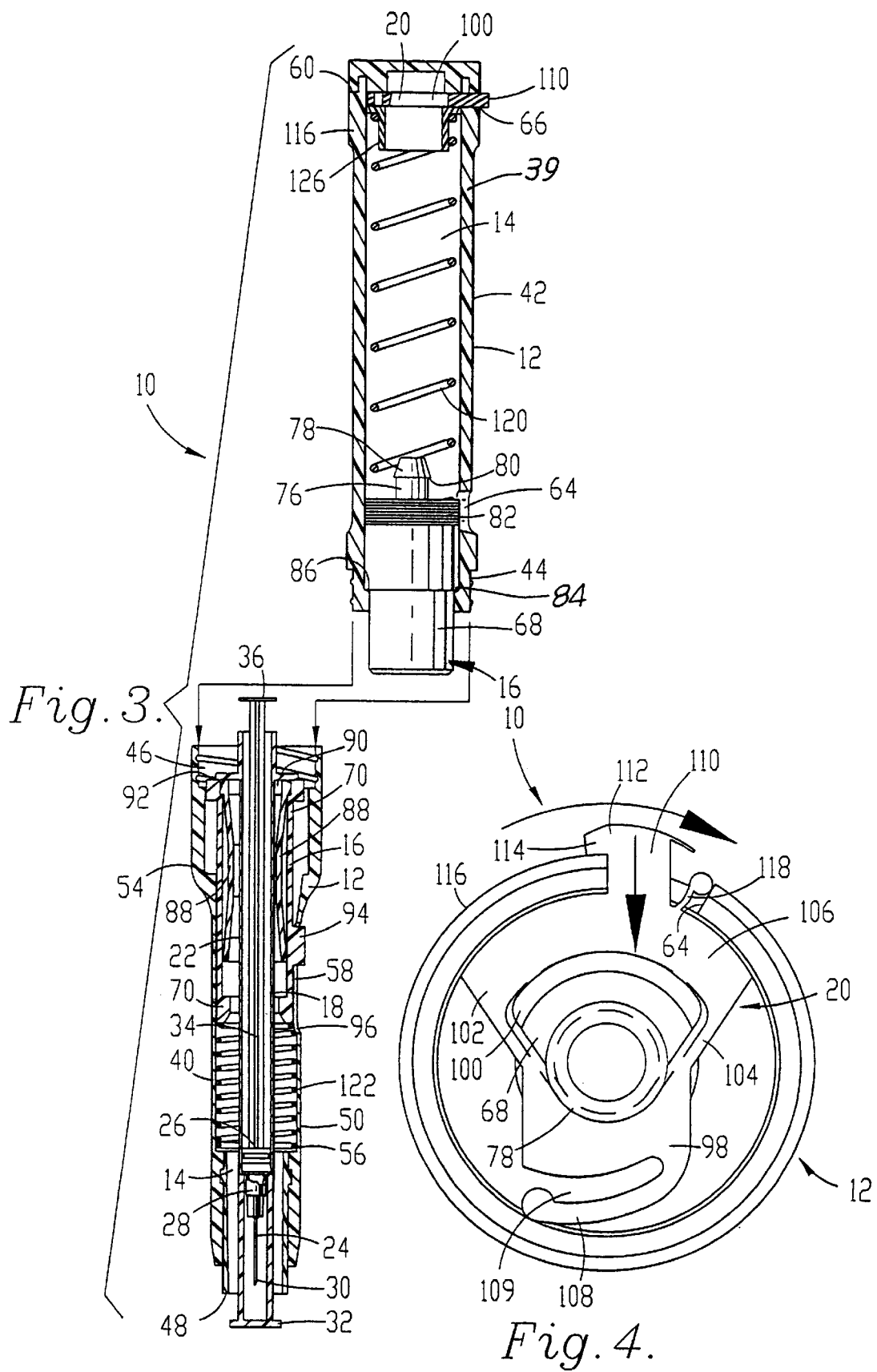

AUTO-INJECTION DEVICE

BACKGROUND OF THE INVENTION

1. Field of the Invention

This invention broadly concerns an device for permitting users to self-inject a medication in a conventional syringe to a preselected depth of penetration by using a simplified triggering mechanism device permitting controlled dosing. More particularly, the present invention is concerned with an automatic injection device with a triggering mechanism which is simple for geriatric users yet includes a safety feature inhibiting premature needle projection and medication discharge.

2. Description of the Prior Art

Auto-injection devices as described herein are used by an individual to self-administer a liquid medication through a needle subcutaneously. These devices help an individual to administer the medication by pushing or driving the needle through the skin and then expressing a dosage of the medication. It can be appreciated that such devices help alleviate the fear associated with injecting oneself and provide a convenience in regard to the accuracy of the dosing.

To this end, a number of different auto-injection devices have been developed. These include the devices shown in U.S. Pat. Nos. 5,137,516 and 5,425,715. These devices provide for an injection from a medication received in an ampule or cartridge assembly. Typically, such devices are first cocked, positioned, and then triggered to administer a desired quantity of medication. The '516 patent operates by actuation of a trigger in combination with movement of two separate parts to prevent accidental actuation. However, both of these devices use a preloaded cartridge or ampule and are not readily adaptable to use with a conventional syringe. This has certain disadvantages in the types of medication which can be obtained and dispensed, as the cartridges or ampules cannot be locally filled by a pharmacist and are not adapted for receiving a commonly available syringe.

Another auto-injection device which can be used with a commercially available cartridge or syringe is shown in U.S. Pat. No. 5,358,489. This device is useful for administering medication but is difficult to handle and use, as a separate tool such as a screwdriver must be employed for recocking and a protective cap may not be retained on the tip of the needle until the desired moment of use. Thus, the '489 device is not well equipped for storage in a ready to use condition for treatment of male impotence by injection or other therapies requiring simplicity of operation and convenience of storage.

It is generally preferable to refrain from "re-capping" a syringe after an injection has been administered because there remains some risk of cross-contamination if the user's hand slips and their finger is stuck by the needle. However, replacement of the cap in self-injection devices may be desired where there are inadequate facilities for safe storage of medical sharps, or where the syringe might be set aside for some time, with the result that the user may forget that the needle is exposed.

There has thus developed a need for an auto-injection device capable of use with a standard syringe which can be filled by a local pharmacist and which can be stored with the cap in place to inhibit undesired needle "sticks".

There has also developed a need for an auto-injection device which is easy to use by geriatric patients and yet resists undesired or premature needle exposure and medication expression.

There has further developed a need for an auto-injection device which can be partially disassembled for loading and cocked, all without the need for additional tools.

There is a further need for an auto-injection device which has a trigger which is readily accessible, yet is safe to use and has a simple and inexpensive construction.

There is an additional need for an auto-injection device which includes a feature to enhance safe replacement of a needle on the syringe contained therein.

SUMMARY OF THE INVENTION

These needs are largely met by the auto-injection device of the present invention which is adapted to receive a conventional syringe with the needle cap in place both during loading and up until administration. The device hereof is easy to use and includes a unique trigger which requires displacement along two axes in order to actuate the injection sequence.

The invention hereof broadly includes a body or barrel presenting an internal cavity for receiving a syringe therein. The barrel cavity presents a longitudinal axis adapted for receiving a syringe therein. The barrel presents an open front end for positioning against a patient's body and through which the needle of the syringe may project, and a rear end. A driver is positioned within the barrel for longitudinal shifting within the cavity, the driver being configured to carry a conventional syringe. The driver includes a catch at the rearward end thereof adapted to engage a release mounted on the barrel. The release includes a resilient member for biasing the release to a position engaged with the catch on the driver. The release is configured and mounted on the barrel to require movement of the release along the surface of the barrel as well as depression into the cavity in order to disengage from the catch and release the driver for injecting the contents of the syringe.

Advantageously, the auto-injection device hereof has a barrel separable into two separate sections. The driver is also provided in two components, including a syringe receiver mounted in the forward section of the barrel and a pusher positioned in the normally rearward section of the barrel. The two sections of the barrel are complementally configured to permit an elongated neck on the forward section to enter the cavity of the rearward section to thereby urge the pusher rearwardly until the catch on the pusher engages the release. The syringe receiver is provided with a plurality of inwardly directed fingers which hold the syringe in a central, longitudinally aligned position, but permit insertion and withdrawal of the syringe with the syringe cap retained thereon. The syringe receiver is also provided with a button which projects into a slot in the barrel to permit manual shifting of the syringe to remove or replace the cap on the syringe. The slot includes a recess which holds the button and thus the syringe in a retracted position within the cavity of the barrel.

A spring is provided to push the driver forwardly when released after cocking. A second spring, of a lesser spring force, is provided to urge the syringe receiver rearwardly into a position normally placing the tip of the syringe needle rearwardly of the front end of the barrel when the device is uncocked.

The release is preferably provided with a trigger which extends radially outwardly of the exterior surface of the barrel. The trigger is preferably integral with a resilient arm which biases the trigger outwardly, and also includes a resilient stem for biasing the trigger to a position opposite the exterior surface of the barrel and out of alignment with a trigger access. The release further includes a notch in which the catch of the driver is received when the device is cocked. In order to actuate the device and move the syringe forwardly within the cavity, the user must push the trigger along the surface of the barrel and then through the trigger access to overcome the resilient arm and move the notch to release the catch. Preferably, indicia is provided on the driver which is visible through a window defined in the barrel, whereby the user can identify when the device is cocked.

As so configured, the auto-injection device hereof is particularly easy to use. By separating the threaded connectors on the two barrel sections, a conventional syringe may be inserted into the syringe receiver with its needle or cannula pointing forwardly and its plunger extending rearwardly. The neck of the forward section is then inserted into the cavity of the rearward section and the pusher of the driver urged rearwardly until the catch is held in the notch of the release. The forward section is then threaded on the rearward section and may be stored until use is desired. In order to inject the medication in the syringe, the user pushes the button forwardly along the slot, which extends the needle and cap into a position whereby the user may manually remove the cap. The second spring then moves the needle back within the cavity.

Administering the injection is accomplished after the front end is placed on the desired injection site. The user is inhibited from inadvertently triggering the device by the two-direction movement of the trigger necessary to release the driver. Once the trigger is moved along the exterior surface of the barrel until it is over the access opening, it may be depressed to move the notch and release the catch on the pusher. The pusher then moves forwardly against the thumbbutton of the syringe plunger, moving the syringe forwardly and pushing the cannula under the skin of the patient until the syringe is stopped from further movement within the cavity. After syringe movement is stopped, the pusher continues its forward movement, overcoming the resistance of the liquid medication in the syringe to express the medication from the cannula. Once the medication is injected into the patient, the needle is withdrawn and the cap replaced on the needle with the syringe receiver shifted rearwardly and the button thereon held in the recess.

It may be readily appreciated that the device hereof permits a simplified injection procedure with safeguards against undesired actuation of the mechanism in a simple, inexpensive device using conventional syringes. Thus, the device hereof presents significant advantages over more complicated auto-injection devices requiring specialized cartridges, additional tools, or which risk premature needle exposure.

These and other benefits of the present invention will be readily evident to those skilled in the art with reference to the drawing and detailed description set forth below.

BRIEF DESCRIPTION OF THE DRAWINGS

FIG. 1 is a perspective view of the auto-injection device hereof showing the device in the uncocked position carrying a syringe with the needle cap projecting from the front end of the device;

FIG. 2 is a vertical cross-sectional view similar to FIG. 1, showing the syringe within the barrel of the device and the driver in the cocked position;

FIG. 3 is a vertical cross-sectional view of the device hereof showing the first front section and second rear section of the barrel separated with the syringe carried by the syringe receiver of the driver; and FIG. 4 is an enlarged vertical end elevational view of the device hereof taken rearwardly of the release facing toward the front of the device with the end cap removed, showing the catch of the pusher held in the notch of the release.

DESCRIPTION OF THE PREFERRED EMBODIMENT

Referring now to the drawing, an auto-injection device 10 showing the preferred embodiment of the present invention broadly includes a barrel 12 presenting a longitudinally extending cavity 14. A driver 16 and a syringe 18 are received in the cavity 14, the barrel mounting a release 20 for actuating the device 10 to inject a liquid medication from the syringe 18.

In greater detail, the syringe 18 is of conventional construction and is commercially available from a variety of sources, such as, for example, a 1 cc syringe offered by Becton-Dickenson. The syringe includes a body 22 mounting a needle 24 and receiving a plunger 26. The needle 24 includes a needle hub 28 and a cannula 30 for penetrating the skin and injecting the liquid medication contained in the syringe body 22. Such medication may include, for example, insulin for treating diabetes, a vasodilator for treating male sexual dysfunction, or other liquids as desired. The needle cannula receives thereon a cap 32 which extends over the cannula 30 and is removably mounted on the needle hub 28. The plunger 26 includes a shaft 34 presenting a stopper at one end thereof and received within the body 22, and a driving surface 36 at the rear end, the driving surface 36 normally used as a thumb rest. The body 22 is tubular and may present scale markings on the surface thereof to indicate the volume of liquid in the syringe. A finger flange 38 extends laterally from the rear end of the body 22.

The barrel 12 includes a first front section 40 and a second rear section 42 which are longitudinally aligned along a longitudinal axis A when threadably interconnected as shown in FIG. 1, and separable into two sections as shown in FIG. 3. The rear section 42 includes a threaded insert 44 and the front section 40 presents a threaded sleeve 46 at its rear end for receiving the threaded insert 44. The front section 40 also presents a front end 48 which is open and has a diameter sufficient to permit the passage of the cap 32 on the needle 24 to pass therethrough. The front section 40 also has a neck 50 which extends rearwardly from the front end 48 and is sufficiently narrow to allow insertion of the neck 50 into the cavity 14 of the rear section 42. A collar 52 is positioned rearwardly of neck 50 on the front section 40, the collar 52 presenting an enlarged internal diameter relative to the internal diameter of the neck 50, and having a rim 54 where the diameter of the cavity 14 internally of the collar 52 narrows to the diameter of the neck 50. The internal diameter of the cavity 14 interiorly of the neck 50 further narrows at edge 56 located between front end 48 and rim 54. A longitudinally extending slot 58 is provided through the front section 40, the slot 58 communicating with a laterally displaced recess 59.

The rear section 42 presents a rear end 60 mounting a endcap 62 thereon. A window 64 is provided in the rear section 42 for viewing into the cavity 14. A trigger access 66 is defined at the rear end of the barrel 12 just forwardly of endcap 62. The endcap 62 may be snap-fitted onto the rear end 60 of the rear section or, more preferably, adhesively secured thereto.

The plunger 26 is axially shiftable along the longitudinal axis A within the cavity 14 and includes a pusher 68 shiftably located in the rear section 42 and a syringe receiver 70 shiftably located in the front section 40. The pusher includes a base 72 and a cylindrical wall 74 having a diameter preferably sufficient to receive the driving surface 36 of the syringe plunger 26 therein. A stem 76 projects rearwardly from base 72 and terminates in a frustoconically shaped catch 78 having a margin 80. The wall 74 extends both forwardly and rearwardly from base 72 as illustrated in FIG. 2. The pusher 68 includes indicia 82, such as a colored band, which is visible through the window 64 when the pusher is shifted forwardly as shown in FIG. 3. When shifted forwardly, a circumferentially extending lug 84 on the pusher 68 engages an internal rim 86 inward of the threaded insert 44 to limit forward travel of the pusher 68.

The syringe receiver 70 is not only longitudinally shiftably received in the cavity 14 but may also be shifted circumferentially relative to barrel 12. The syringe receiver 70 includes a plurality of circumferentially arrayed flexible alignment fingers 88 which collectively engage and center the body 22 of syringe 18. The rearward end of the syringe receiver 70 presents a breech 90 including a margin 92 against which finger flanges 38 of the syringe 18 engage. The syringe receiver further presents an outwardly extending button 94 which projects into and is longitudinally slidably received within slot 58, and may be circumferentially shifted into the recess 59. Recess 59 is configured and sized to receive button 94, and then to hold button 94 against undesired lateral shifting when button 94 is biased forwardly. The forward end of the syringe receiver 70 presents a circular edge 96.

Release 20 is best seen in FIG. 4 and includes a frame 98 having a v-shaped notch 100 centrally located therein. The frame includes a pair of legs 102 and 104 on either side of the notch 100 and a bridge 106 connecting the legs 102, 104. A resilient arm 108 is located opposite the bridge 106 and biases the release 20 located within the cavity 14 of the rear section 42 toward the trigger access 66. The arm 108 is flexible and cantilevered from the main frame 98 presenting a gap 109 therebetween. Trigger 110 extends through the trigger access 66 and presents an enlarged head 112 having a chin 114 projecting circumferentially along the exterior surface 116 of wall 39 of the barrel 12. A resilient reed 118 is located on the opposite side of trigger 110 from chin 114 and also extends into trigger access 66 and biases the trigger 110 to a position as shown in FIG. 4 whereby the chin 114 will engage the exterior surface 116 of the barrel and not pass through the trigger access 66 when the head 112 is only depressed and not first pushed toward reed 118.

The auto-injector device hereof includes a first spring 120 positioned in the cavity 14 of the rear section 42 between the driver 16 and the release 20. The spring 120 is preferably a coil spring which is helically arrayed around the stem 76 of the pusher 68 and extends forwardly to engage base 72 as shown in FIG. 2 and is received within wall 74 when the pusher is in its rearward position. A second spring 122 is located in the cavity 14 between the syringe receiver 70 and the edge 56 on barrel 12 as shown in FIG. 3. Second spring 122 is of a lesser spring coefficient than first spring 120, so that when first and second sections are assembled and the first spring 120 is unloaded and pushing against pusher 68 and syringe 18, the second spring 122 yields and compresses. Second spring 122 is held in position by an alignment member 126 positioned forwardly of release 20.

To use the device 10, the user first unscrews the first front section 40 from the second, rear section 42 and inserts the neck 50 into the cavity 14 of the rear section. The front end 48 then engages the pusher 68 and moves it rearwardly against first spring 120 until the catch 78 is received in notch 100. With the catch 78 engaged in the notch 100, the pusher 68 compresses and loads first spring 120 to the position shown in FIG. 2. A syringe 18 is then inserted into the syringe receiver 70 until the finger flanges 38 engage the breech 90 of the syringe receiver 70. With the syringe thus loaded into the receiver 70, the second spring 122 biases the syringe receiver 70 rearwardly so that the cap 32 and the tip of the cannula 30 is located within the cavity 14 and rearwardly of the front end 48. The front section 40 is then threaded onto the rear section 42 and the device is ready for use. When ready for use, the indicia 82 is not visible in window 64.

When it is desired to administer a dosage of medication contained within the body 22 of the syringe 18, the user first selects the desired location on the skin for positioning of the front end 48 of the barrel 12. The cap 32 is then removed from the syringe 18 by shifting the button 94 along the slot 58 to compress the second spring 122 and move the syringe receiver 70 and syringe 18 forwardly a sufficient difference to permit manual removal of the cap 32 as illustrated in FIG. 1. After the cap 32 has been removed, the button 94 is released and permitted to slide rearwardly, carrying with it the syringe receiver 70. The front end 48 is then placed on the desired target location of the patient's skin. To administer the injection, the user must first shift the head 112 of the trigger 110 toward the reed 118 in a generally circumferential direction as illustrated by the arrow in FIG. 4. This permits the chin 114 on the head 112 to clear the exterior surface 116 of the barrel 12 and lie directly over the trigger access 66. This required lateral movement inhibits undesired or premature actuation of the device 10. After this lateral shifting, the trigger 110 is then depressed in the direction of the second arrow in FIG. 4 to overcome the resistance of resilient arm 108. When the trigger 110 is thus depressed, the v-shaped notch shifts as shown in phantom in FIG. 4 to permit the margin 80 thereon to clear the legs 102 and 104 of the release 20. Once the catch 78 clears the arms and is permitted to move forwardly through notch 100, the first spring moves the pusher 68 forwardly whereby base 72 engages the driving surface 36 on the plunger 26 of the syringe.

The initial resistance of the stopper within the body 22 of the syringe 18 and the fluid resistance of the medication is greater than the spring coefficient of the second spring 122. Thus, the syringe 18 and the syringe receiver 70 move forwardly and compress the second spring 122 in response to forward movement of the pusher 68. The forward movement of the syringe 18 and syringe receiver 70 continue as the cannula 30 penetrates the patient's skin until the syringe receiver 70 is fully shifted forward to compress the second spring 122. Before the pusher 68 is fully forward as illustrated in FIG. 3, the second spring 122 will be fully compressed and the cannula 30 will have penetrated to the predetermined, desired subcutaneous depth. The pusher 68 then continues to its fully forward position as the base 72 pushes against the driving surface 36 and shifts the plunger 26 relative to the syringe body 22 to express the medication from the syringe. Thereafter, the patient withdraws the needle 24 and replaces the cap 32 as illustrated in FIG. 1. To replace the cap 32, the patient preferably moves the button 94 rearwardly and moves the button 94 laterally into recess 59. A nib 124 partially separates the recess 59 from the slot 58, so that when second spring 122 pushes against the syringe receiver 70, the button 94 is held against further forward movement and inhibited from undesired rotational movement into the slot 58. This cause the cannula 30 to be withdrawn into the cavity 14 and rearward of front end 48 while the cap 32 is manually replaced on the syringe. The button 94 can be safely shifted back into the slot 58 after the cap is replaced so that the cap 32 will be in the position shown in FIG. 1.

FIG. 1 illustrates the condition of the device 10 hereof in a discharged position where upon the patient can see the indicia 32 through the window 64. The needle cannula 30 is also illustrated in FIG. 1 to show its position extending beyond the front end 48 of barrel 12. The syringe 18 may be disposed by unscrewing the front and rear sections 40, 42 and withdrawing the syringe rearwardly through the syringe receiver 70 from the front section 40 of the barrel 12.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventor hereby states his intent to rely on the Doctrine of Equivalents to determine and assess the reasonably fair scope of his invention as it pertains to any apparatus not materially departing from but outside the liberal scope of the invention as set out in the following claims.

What is claimed is:

1. An auto-injection device comprising:
    a barrel having a wall with an external surface and defining therein an internal cavity having a longitudinal axis, said barrel having a front end for placement against a patient's skin and a rear end, said wall having a trigger access therethrough;
    a driver shiftably received in said cavity for movement between a forward, uncocked position and a rearward, cocked position and adapted to engage a syringe for longitudinally shiftable movement of the drive and syringe within said barrel, said driver including a catch positioned more proximate said rear end than said front end of said barrel;
    a release carried by said barrel, said release including a resilient member positioned within said cavity and a trigger projecting through said trigger access and biased by said resilient member to a first position on the exterior surface of the barrel adjacent said trigger access, said release being located within said cavity for retaining said catch when said driver is shifted into said cocked position, said trigger including a projection extending axially therefrom and opposing said exterior surface of said barrel and requiring shifting across said exterior surface about said axis and against said resilient member prior to depression of said trigger toward said axis and into said trigger access to shift the release out of engagement with the catch and permit movement of the driver forwardly to the uncocked position.

2. The device as set forth in claim 1, including a first spring positioned in said cavity between said release and said driver for biasing said driver toward the uncocked position.

3. The device as set forth in claim 2, including an alignment member positioned between the release and the first spring for holding said first spring in position within said cavity.

4. The device as set forth in claim 2, said driver including a pusher and a syringe receiver, said pusher including said catch, said receiver being positioned in said cavity relatively more proximate said front end than said pusher and including a central opening adapted to mount the syringe therethrough.

5. The device as set forth in claim 4, wherein said syringe receiver includes a plurality of resilient fingers surrounding a central aperture and adapted for biasing the a syringe placed into said aperture into alignment along said longitudinal axis.

6. The device as set forth in claim 3, said barrel including a retaining rim projecting into said cavity proximate the front end of said barrel, said device including a second spring received in said cavity between said syringe receiver and said retaining rim.

7. The device as set forth in claim 6, wherein said barrel includes a first second and a separate second section detachable from the first section, said pusher being received in said second section, said first section including a neck complementally sized for receipt in the cavity of the first section when said first section is disconnected from said second section and oriented with the front end of the barrel in engagement with said pusher, said neck having a length sufficient to move said pusher of said driver into the cocked position with the catch engaged by the release.

8. The device as set forth in claim 6, wherein said driver is positioned between said first spring and said second spring whereby said second spring is compressed when said first spring is extended with the driver shifted into the uncocked position, and said second spring is extended when said driver is positioned in the cocked position.

9. A device as set forth in claim 8, wherein said barrel includes a longitudinally extending slot through said exterior surface and said syringe receiver includes a button projecting into said slot for permitting shifting of said syringe receiver longitudinally along said barrel.

10. The device as set forth in claim 9, said barrel having a recess communicating with said slot, laterally displaced therefrom, and positioned proximate a rearward end of said slot, said recess being sized for retaining said button therein when said button is shifted laterally from said slot.

11. The device as set forth in claim 1, wherein said release includes structure defining a notch for receiving said catch therein, said trigger being operatively connected to said notch-defining structure for movement of said notch-defining structure in a direction transverse to said longitudinal axis when said trigger is shifted into said trigger access.

12. The device as set forth in claim 11, said release including an arm located within said cavity in engagement with the barrel and positioned diametrically opposite said trigger for biasing said notch-defining structure into a catch-engaging position.

13. The device as set forth in claim 1, said driver including indicia thereon and said barrel including a window for viewing the indicia on said driver only when the driver is shifted into the uncocked position.

14. In combination:
    a syringe having an elongated tube having an open end and a needle mount at the other end, a needle mounted on the needle mount, and a plunger received in the open end and projecting therefrom, said plunger including a stopper, a thumbrest, and a shaft extending between the stopper and the thumbrest; and
    an injector mounting said syringe for shiftable movement therein between an uncocked position with the needle of the syringe extending beyond the injector and a cocked position with the needle received within the injector, said injector including:
- a barrel having a wall with an external surface and defining therein an internal cavity having a longitudinal axis and complementally sized for receiving said syringe therein, said barrel having a front end for placement against a patient's skin and a rear end, said wall having a trigger access therethrough;
- a driver operatively coupled with said syringe and shiftably received in said cavity for movement between a forward, uncocked position with said needle projecting forwardly of said front end and a rearward, cocked position with said needle withdrawn into said cavity, said driver including a catch positioned more proximate to said rear end than said front end of said barrel;

a release carried by said barrel, said release including a resilient member positioned within said cavity and a trigger projecting through said trigger access and biased by said resilient member to a first position on the exterior surface of the barrel adjacent said trigger access, said release being located within said cavity for retaining said catch when said driver shifted into said cocked position, said trigger including structure opposing said exterior surface of said barrel and requiring shifting across said exterior surface about said axis and against said resilient member prior to depression of said trigger toward said axis and into said trigger access to shift the release out of engagement with the catch and permit movement of the driver forwardly to the uncocked position.

15. The combination of claim 14, including a protective cap mounted on said syringe over said needle, said cap being sized to project from said front end of said barrel when said driver is in the uncocked position and normally withdrawn within said cavity rearwardly from said front end when said plunger is in the cocked position, and a button connected to said driver and projecting through a slot to be accessible exteriorly of said barrel for shifting said syringe forwardly within said cavity when said plunger is shifted into said cocked position for exposing said cap forwardly of said front end.

16. The combination of claim 15, said barrel having a recess communicating with said slot, laterally displaced therefrom, and positioned proximate a rearward end of said slot, said recess being sized for retaining said button therein when said button is shifted laterally from said slot into said recess.

17. The combination of claim 14, including indicia on said driver and a window in said barrel located over said indicia when said driver is in the uncocked position.

18. The combination of claim 14, wherein said driver includes a pusher and a syringe receiver and said barrel includes a first section and a separate second section detachable from said first section and carrying said pusher, said first section including a neck complementally sized for receipt in the cavity of the first section when said first section is detached from said second section and oriented with the front end of the barrel in engagement with said pusher, said neck having a length sufficient to move said pusher of said driver into the cocked position with the catch engaged by the release.

19. The device as set forth in claim 14, including a first spring positioned in said cavity between said release and said driver for biasing said driver toward the uncocked position, and a second spring received in said cavity between said front end and said driver.

20. The device as set forth in claim 19, including an alignment member positioned between the release and the first spring for holding said first spring in position within said cavity.

* * * * *